United States Patent
Paik et al.

(10) Patent No.: US 7,216,543 B2
(45) Date of Patent: May 15, 2007

(54) MASS MEASUREMENT SYSTEM AND METHOD USING MEASUREMENT OF FREQUENCY SHIFT OF VIBRATOR

(75) Inventors: Hong Yul Paik, Daejeon (KR); Hae Jin Choi, Seoul (KR); Gi Hyuk Choi, Daejeon (KR); Jong Woo Kim, Daejeon (KR); Youn Kyu Kim, Daejeon (KR)

(73) Assignee: Korea Aerospace Research Institute, Daejeon (KR)

( * ) Notice: Subject to any disclaimer, the term of this patent is extended or adjusted under 35 U.S.C. 154(b) by 145 days.

(21) Appl. No.: 11/180,193

(22) Filed: Jul. 13, 2005

(65) Prior Publication Data
US 2006/0015268 A1    Jan. 19, 2006

(30) Foreign Application Priority Data
Jul. 15, 2004  (KR) ............... 10-2004-0055193

(51) Int. Cl.
*G01N 29/12* (2006.01)
(52) U.S. Cl. .................. 73/579; 73/32 A; 73/657
(58) Field of Classification Search .......... 73/579, 73/32 A, 54.26, 580, 649, 657; 310/321
See application file for complete search history.

(56) References Cited

U.S. PATENT DOCUMENTS

| | | | | |
|---|---|---|---|---|
| 4,789,804 A * | 12/1988 | Karube et al. ............. 310/311 |
| 5,837,885 A * | 11/1998 | Goodbread et al. ......... 73/32 A |
| 6,370,939 B2 * | 4/2002 | Smith et al. .............. 73/19.03 |
| 6,840,123 B2 * | 1/2005 | Takeuchi et al. ........... 73/865 |
| 6,848,299 B2 * | 2/2005 | Paul et al. ................ 73/64.53 |
| 6,895,829 B2 * | 5/2005 | Takeuchi et al. ........... 73/865 |
| 7,165,452 B2 * | 1/2007 | Kobayashi ................ 73/580 |
| 2005/0087019 A1 * | 4/2005 | Face ...................... 73/649 |

FOREIGN PATENT DOCUMENTS
JP    2161323    6/1990

* cited by examiner

*Primary Examiner*—Hezron Williams
*Assistant Examiner*—Jacques M. Saint-Surin
(74) *Attorney, Agent, or Firm*—Volpe and Koenig P.C.

(57) ABSTRACT

The present invention relates to a mass measurement system and method capable of precisely measuring the mass of a sample in a gravity-free environment. The mass measurement system using measurement of frequency shift of a vibrator according to the present invention includes a vibrator vibrating at a predetermined resonance frequency with a mass of a sample added thereto, a frequency counter for measuring a resonance frequency of the vibrator caused by vibration, a standard mass database for storing therein known standard masses and standard mass frequency shifts corresponding to variation in the standard masses, and a main controller for calculating a sample mass frequency shift corresponding to the added sample mass on the basis of the resonance frequency received from the frequency counter, searching the standard mass frequency shifts stored in the standard mass database, comparing the calculated sample mass frequency shift with the searched standard mass frequency shifts, extracting a predetermined standard mass, outputting the extracted standard mass as the mass of the sample, and controlling the entire system. Accordingly, the present invention can precisely measure the mass of a small-sized sample, in particular, an animal sample, in a gravity-free environment.

14 Claims, 5 Drawing Sheets

MASS MEASUREMENT SYSTEM AND METHOD USING MEASUREMENT OF FREQUENCY SHIFT OF VIBRATOR

BACKGROUND OF THE INVENTION

1. Field of the Invention

The present invention relates, in general, to a mass measurement system and method and, more particularly, to a mass measurement system and method using the measurement of the frequency shift of a vibrator, which measure a frequency shift according to the variation of mass added to a vibrator, thus precisely measuring the mass of a sample, especially in a gravity-free environment.

2. Description of the Related Art

The present invention relates a mass measurement system and method in a gravity environment, as well as a gravity-free environment, but, hereinafter, an embodiment implemented, in particular, in a gravity-free environment is described.

Generally, the inside of a spacecraft traveling in space is in a micro gravity environment having little gravity, or in a gravity-free environment. In order to measure the mass of a sample, which is a space experiment object, such as a rat, in a spacecraft having a micro gravity or gravity-free environment, the mass of the sample is measured using a device generally known as a so-called "space mass measuring device", not a typical balance for measuring mass in a gravity field.

Hereinafter, a conventional mass measurement device in a gravity-free environment, which is designated as a so-called "space mass measuring device", is described.

FIG. 1 is a conceptual configuration view showing conventional mass measurement in a gravity-free environment.

The conventional mass measurement in a gravity-free environment of FIG. 1 is performed using a spring 10 having a predetermined elastic modulus k, a sample S connected to the spring 10, and a frequency counter (not shown) connected to the sample S to measure the frequency of the spring 10.

In a mass measurement method performed by the conventional mass measurement device in a gravity-free environment, external force is applied to the sample S to cause vibration, so that the frequency of the sample S connected to the spring 10 is measured by the frequency counter (not shown).

Further, the mass of the sample S is measured using a calculation program based on the measured frequency of the spring 10 and the elastic modulus k of the spring 10.

However, the above-described conventional mass measurement method in a gravity-free environment causes the following problems.

First, the mass of the sample S measured by the conventional mass measurement technology in a gravity-free environment in FIG. 1 has a large error because it is difficult to precisely measure a vibration period due to the damping effect of the measurement device itself.

Second, if the above-described mass measurement method in a gravity-free environment is used, there is a problem in that repeated measurements must be performed for a long period of time so as to perform precise measurement.

Third, a vibration system itself using the mass measurement device of FIG. 1 is a non-linear system, so that it is very difficult to obtain the mass of a sample S on the basis of a vibration period, and measurements are subject to error.

Further, according to the conventional mass measurement method currently used in a spacecraft, it is known that an error of about 1% occurs at the time of measurement, so that the method is not suitable for precise measurement and it has actually been used for a method of roughly measuring the weight of an astronaut.

Fourth, the conventional mass measurement method is limitedly used to approximately measure large masses such as the weight of an astronaut (for example, a mass of about 100 kg). That is, there occurs the problem in that the conventional mass measurement method is not suitable for the precise measurement of a small mass (for example, a mass of 5 kg or less) for space experiments, the necessity of which is recently increasing, for example, precise measurement having an error of 1% or less.

Accordingly, since precise measurements prior or subsequent to an experiment on a space experiment sample are mainly performed on earth, a large inconvenience is caused, thus the precision and efficiency of space experiments are greatly limited.

SUMMARY OF THE INVENTION

Accordingly, the present invention has been made keeping in mind the above problems occurring in the prior art, and an object of the present invention is to provide a mass measurement system and method using the measurement of the frequency shift of a vibrator, which measure the resonance frequency shift of a vibrator according to the addition of a sample, and extract a standard mass value corresponding to the measured resonance frequency shift from a standard mass database, thus precisely measuring the mass of the sample.

Another object of the present invention is to provide a mass measurement system and method using the measurement of the frequency shift of a vibrator according to a mass variation, in which the vibrator is implemented as an electro-dynamic vibrator that can be used in a wide frequency band, can generate an arbitrary vibration level and can be easily controlled, wherein in particular, the vibrator is a piezo vibrator that generates a high frequency vibration and has a low vibration amplitude, so that stress is not given to a main sample, such as a rat, thus improving the precision of measurement.

In order to accomplish the above objects, the present invention provides a mass measurement system using measurement of frequency shift of a vibrator, comprising a vibrator vibrating at a predetermined resonance frequency with a mass of a sample added thereto, a frequency counter for measuring a resonance frequency of the vibrator caused by vibration, a standard mass database for storing therein known standard masses and standard mass frequency shifts corresponding to variation in the standard masses, and a main controller for calculating a sample mass frequency shift corresponding to the added sample mass on the basis of the resonance frequency received from the frequency counter, searching the standard mass frequency shifts stored in the standard mass database, comparing the calculated sample mass frequency shift with the searched standard mass frequency shifts, extracting a predetermined standard mass, outputting the extracted standard mass as the mass of the sample, and controlling the entire system.

Preferably, the mass measurement system may further comprise a vibration controller for outputting a control signal to the vibrator and controlling the vibration of the vibrator under the control of the main controller.

Preferably, the vibrator may be implemented with an electro-dynamic vibrator.

Preferably, the electro-dynamic vibrator may be implemented with a piezo vibrator.

Preferably, the electro-dynamic vibrator may be implemented with a quartz vibrator.

Preferably, the electro-dynamic vibrator may be implemented with a ceramic vibrator.

Preferably, the electro-dynamic vibrator may be implemented with a lithium sulphate vibrator.

Further, the present invention provides a mass measurement method using measurement of frequency shift of a vibrator, comprising the steps of vibrating a vibrator with a mass of a sample added thereto under control of a vibration controller, measuring a resonance frequency of the vibrator caused by vibration using a frequency counter, calculating a sample mass frequency shift corresponding to the added sample mass on the basis of the measured resonance frequency, searching standard mass frequency shifts that are stored in a standard mass database and correspond to variation in standard masses, and comparing the searched standard mass frequency shifts with the calculated sample mass frequency shift, determining whether a standard mass frequency shift identical to the calculated sample mass frequency shift exists among the searched standard mass frequency shifts by comparison, extracting a standard mass, corresponding to the identical standard mass frequency shift, as the mass of the sample if the identical standard mass frequency shift exists as a result of determination, and displaying the extracted standard mass.

DESCRIPTION OF THE PREFERRED EMBODIMENTS

Hereinafter, a mass measurement system and method using the measurement of the frequency shift of a vibrator according to embodiments of the present invention will be described in detail with reference to the attached drawings.

The present invention relates to a mass measurement system and method that can be applied both to gravity-free and gravity environments. However, in the present specification, embodiments implemented, in particular, in a gravity-free environment are described.

Figure 1:
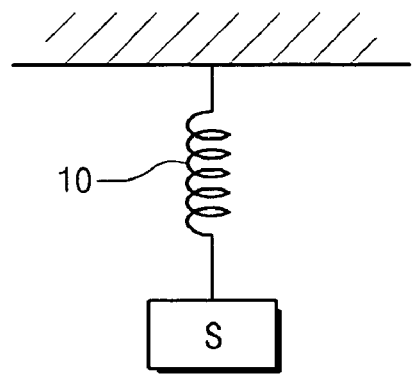
FIG. 1 is a conceptual configuration view of conventional mass measurement in a gravity-free environment.
Figure 2:
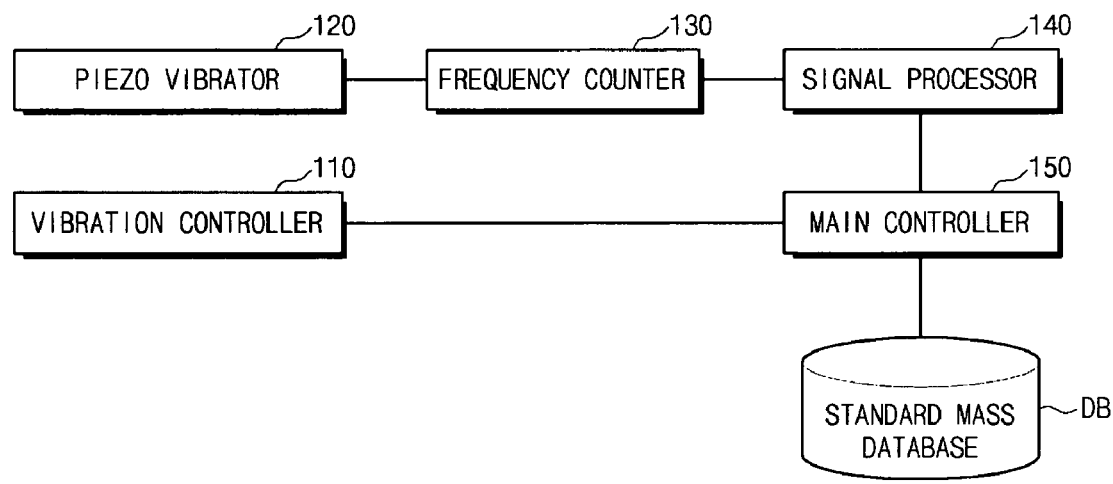
FIG. 2 is a block diagram of a mass measurement system in a gravity-free environment according to an embodiment of the present invention.

FIG. 2 is a block diagram of a mass measurement system using the measurement of the frequency shift of a vibrator according to an embodiment of the present invention.

As shown in FIG. 2, the mass measurement system according to an embodiment of the present invention includes a piezo vibrator 120, a frequency counter 130, a signal processor 140, a standard mass database DB, a main controller 150 and a vibration controller 110.

The piezo vibrator 120 vibrates at a predetermined resonance frequency corresponding to a voltage input from the vibration controller 110. The piezo vibrator 120 vibrating to correspond to the input voltage in this way has a natural resonance frequency $f_o$ that has been previously determined. If a sample S having a mass of $m_x$ is added to the piezo vibrator 120, the shift of the resonance frequency occurs in proportion to the mass $m_x$ of the added sample S.

If the resonance frequency of the piezo vibrator 120 vibrating with the sample S having a mass of $m_x$ added thereto is $f_x$, the shift of the resonance frequency according to the addition of the sample S having a mass of $m_x$ is $\Delta f_x = f_o - f_x$.

Hereinafter, $f_x$ is designated as a "resonance frequency according to the addition of a sample" or simply as a "resonance frequency $f_x$". Further, $\Delta f_x$ is designated as a "resonance frequency shift according to the addition of a sample" or simply as a "resonance frequency shift $\Delta f_x$".

The frequency counter 130 measures the resonance frequency of the piezo vibrator 120.

The signal processor 140 amplifies the resonance frequency signal, which is an analog signal measured by the frequency counter 130, and Analog/Digital (A/D) converts the amplified signal.

In the standard mass database DB, the resonance frequency shifts $\Delta f_1, \Delta f_2, \Lambda, \Delta f_N$ of the piezo vibrator 120 according to the addition of known standard masses $m_1, m_2, \Lambda, m_N$ within a predetermined range are stored. In this case, $\Delta f_1 = f_0 - f_1, \Delta f_2 = f_0 - f_2, \Lambda, \Delta f_N = f_0 - f_N$ is satisfied. The "standard mass" denotes the mass of a standard sample, which has been precisely and exactly measured at ground level and is known.

Further, hereinafter, the "resonance frequency shift according to the addition of standard mass" is denoted by $\Delta f_{i, j=1,2,\Lambda,N}$, and is designated simply as a "resonance frequency shift $\Delta f_i$".

The main controller 150 calculates the resonance frequency shift $\Delta f_x$ on the basis of the resonance frequency $f_x$ received from the signal processor 140, searches "resonance frequency shifts according to the addition of standard masses" stored in the standard mass database DB, compares the searched "resonance frequency shifts according to the addition of standard masses" with the calculated resonance frequency shift $\Delta f_x$ of the sample S, and extracts a "predetermined standard mass". Further, the main controller 150 outputs the extracted standard mass as the mass of the sample. Further, the main controller 150 controls the operation of the entire system.

The "predetermined standard mass" means a standard mass corresponding to an identical "resonance frequency shift value according to the addition of standard mass" if a resonance frequency shift identical to the calculated resonance frequency shift A exists among the searched "resonance frequency shifts according to the addition of standard masses", and means a standard mass corresponding to a "resonance frequency shift according to the addition of standard mass" having a minimum difference with respect to the calculated resonance frequency shift value if an identical resonance frequency shift does not exist.

Further, the vibration controller 110 outputs a control signal to the piezo vibrator 120 and controls the vibration of the vibrator under the control of the main controller 150.

Figure 3:
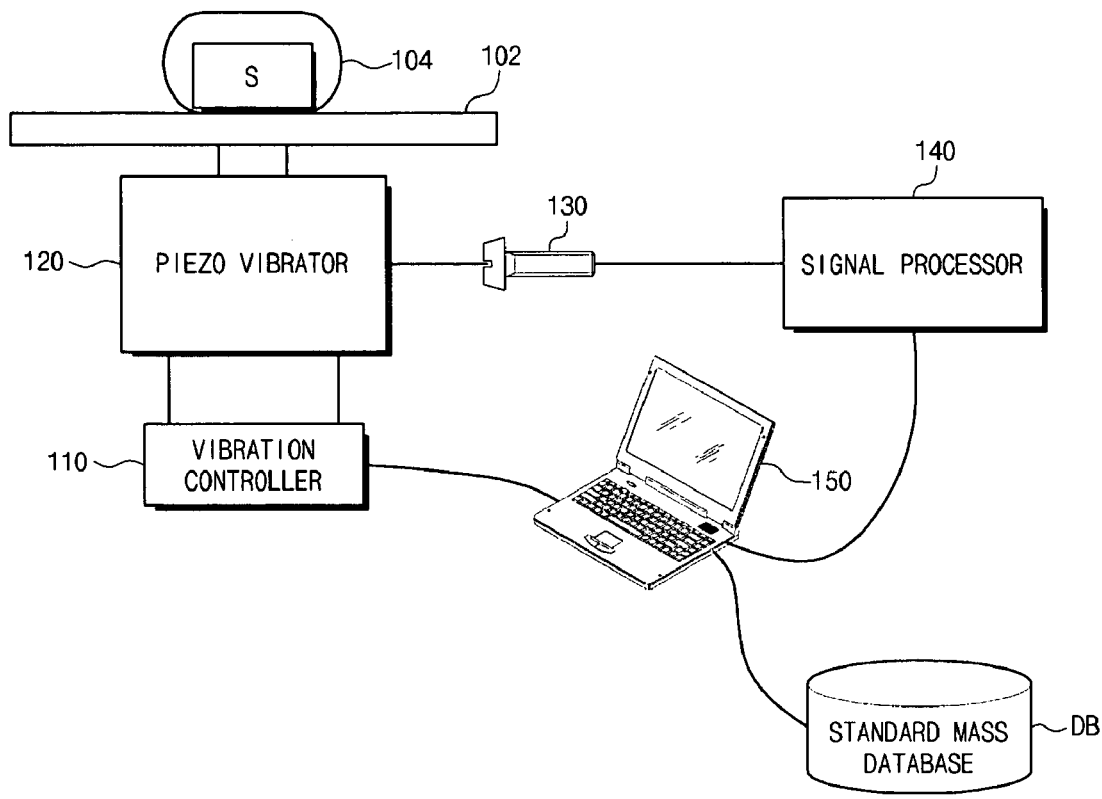
FIG. 3 is a diagram showing the construction of the system of FIG. 2.

FIG. 3 is a diagram showing the construction of the system of FIG. 2.

The mass measurement system using the measurement of the frequency shift of a vibrator according to the present invention preferably further includes a fixing container 104.

The fixing container 104 contains the sample S and prevents the sample from being removed from the piezo vibrator 120 due to a vibration in a gravity-free environment. If the sample S is an animal, such as a rat, the fixing container 104 is especially useful to prevent the animal sample from being removed from the piezo vibrator 120 due to a gravity-free state.

The mass measurement system using the measurement of the frequency shift of a vibrator according to the present invention preferably further includes a support plate 102 interposed between the piezo vibrator 120 and the fixing container 104 and fastened to the piezo vibrator 120 and the fixing container 104, respectively.

The support plate 102 is a component for easily fastening the sample S or the fixing container 104 to the piezo vibrator 120 if the size of the sample S is greater than the area of the piezo vibrator 120 and it is difficult to place the sample S or the fixing container 104 on the piezo vibrator 120.

Figure 4:
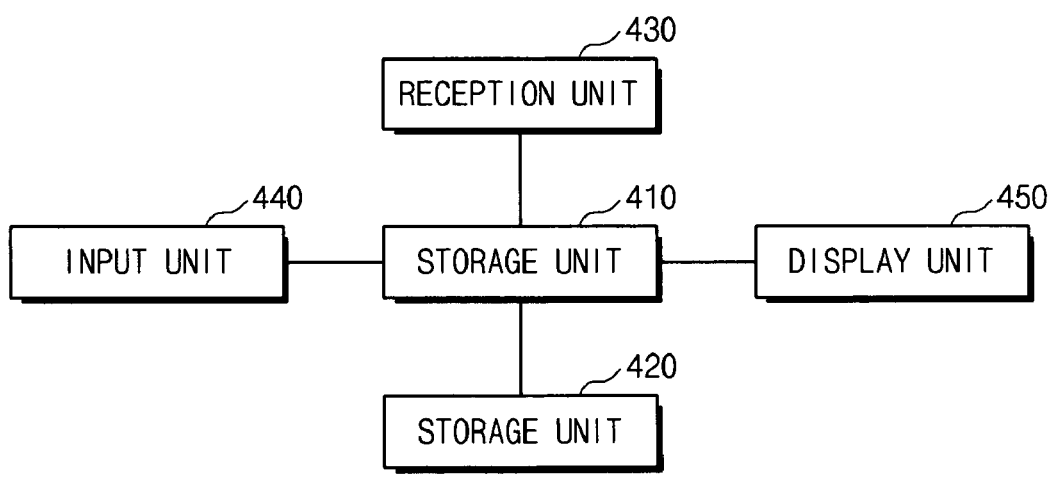
FIG. 4 is a detailed block diagram of a main controller of FIG. 2 according to an embodiment of the present invention.

FIG. 4 is a detailed block diagram of the main controller 150 of FIG. 2 according to an embodiment of the present invention.

As shown in FIG. 4, the main controller 150 according to an embodiment of the present invention includes a reception unit 430, a storage unit 420, a control unit 410, a display unit 450 and an input unit 440.

The reception unit 430 receives the resonance frequency $f_x$ of the piezo vibrator 120 with the sample S added thereto, from the signal processor 140.

The storage unit 420 stores a program for calculating the resonance frequency shift $\Delta f_x$ on the basis of the resonance frequency $f_x$, received from the reception unit 430, searching "resonance frequency shifts according to the addition of standard masses" stored in the standard mass database DB, comparing the calculated resonance frequency shift $\Delta f_x$ with the searched "resonance frequency shifts according to the addition of standard masses", and extracting "predetermined standard mass".

The control unit 410 reads the program stored in the storage unit 420 to execute calculation, search, comparison and extraction, and controls the entire system.

The display unit 450 displays standard mass extracted under the control of the control unit 410.

The input unit 440 is a user interface for receiving a user's command.

Figure 5:
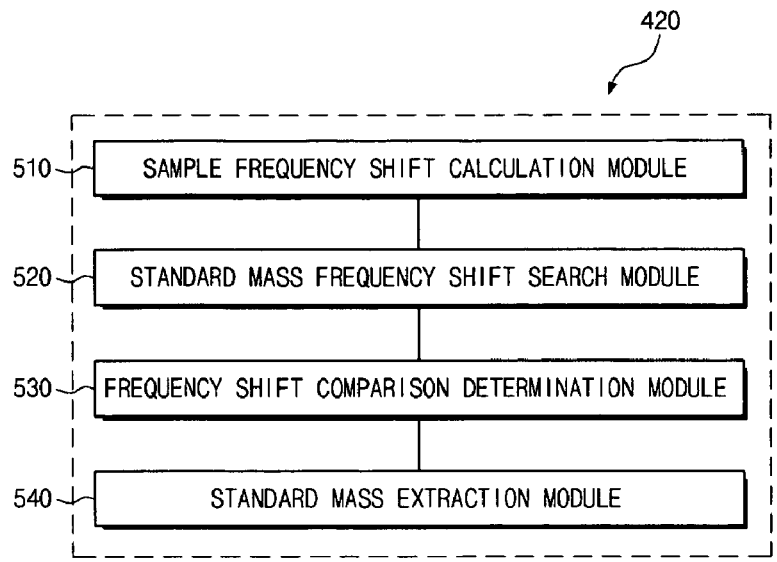
FIG. 5 is a detailed block diagram of a storage unit of FIG. 4.

FIG. 5 is a detailed block diagram of the storage unit 420 of FIG. 4.

As shown in FIG. 5, the storage unit 420 includes a sample frequency shift calculation module 510, a standard mass frequency shift search module 520, a frequency shift comparison determination module 530 and a standard mass extraction module 540.

The sample frequency shift calculation module 510 calculates the resonance frequency shift $\Delta f_x$ on the basis of the resonance frequency $\Delta f_x$ received from the reception unit 430.

The standard mass frequency shift search module 520 searches resonance frequency shifts $\Delta f_i$ according to the addition of standard masses stored in the standard mass database DB.

The frequency shift comparison determination module 530 compares the search results obtained by the standard mass frequency shift search module 520 with the calculation result for the resonance frequency shift $\Delta f_x$ by the sample frequency shift calculation module 510, and determines whether a resonance frequency shift identical to the calculated resonance frequency shift $\Delta f_x$ exists among the searched resonance frequency shifts $\Delta f_i$ according to the addition of standard masses.

The standard mass extraction module 540 extracts a standard mass corresponding to an identical resonance frequency shift value according to the addition of standard mass if the resonance frequency shift identical to the calculated resonance frequency shift $\Delta f_x$ exists among the searched resonance frequency shifts $\Delta f_i$ as a result of the determination by the frequency shift comparison determination module 530, and extracts a standard mass corresponding to a resonance frequency shift having a minimum difference with respect to the calculated frequency shift value if an identical resonance frequency shift does not exist among the resonance frequency shifts $\Delta f_i$.

Figure 6:
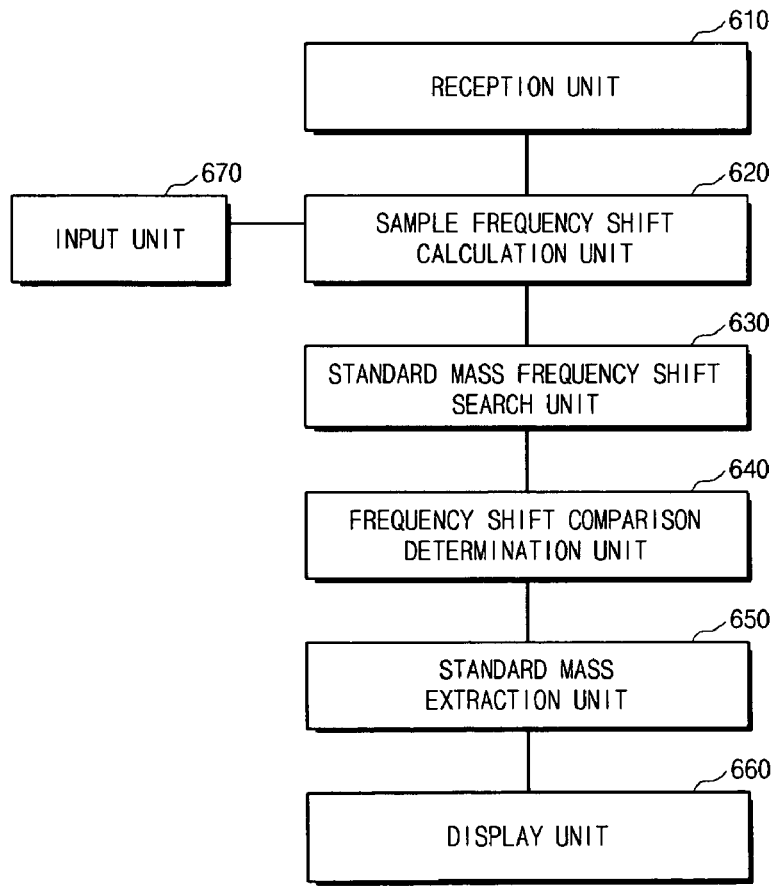
FIG. 6 is a detailed block diagram of the main controller of FIG. 2 according to another embodiment of the present invention.

FIG. 6 is a detailed block diagram of the main controller 150 of FIG. 2 according to another embodiment of the present invention.

As shown in FIG. 6, the main controller according to another embodiment of the present invention includes a reception unit 610, a calculation unit 620, a standard mass frequency shift search unit 630, a frequency shift comparison determination unit 640, a standard mass extraction unit 650, a display unit 660 and an input unit 670.

The reception unit 610 receives the resonance frequency $f_x$ of the piezo vibrator 120 from the signal processor 140.

The sample frequency shift calculation unit 620 calculates a resonance frequency shift $\Delta f_x$ on the basis of the resonance frequency $f_x$ received from the reception unit 610.

The standard mass frequency shift search unit 630 searches resonance frequency shift values $\Delta f_i$ according to the addition of standard masses, stored in the standard mass database DB.

The frequency shift comparison determination unit 640 compares search results obtained by the standard mass frequency shift search unit 630 with the calculation result obtained by the sample frequency shift calculation unit 620, and determines whether a resonance frequency shift identical to the calculated resonance frequency shift $\Delta f_x$ exists among the searched resonance frequency shifts $\Delta f_i$ according to the addition of standard masses.

The standard mass extraction unit 650 extracts a standard mass corresponding to an identical resonance frequency shift according to addition of standard mass if the resonance frequency shift identical to the calculated resonance frequency shift $\Delta f_x$ exists among the searched resonance frequency shifts $\Delta f_i$ as a result of determination by the frequency shift comparison determination unit 640, and extracts a standard mass corresponding to a resonance frequency shift having a minimum difference with respect to the calculated frequency shift value if an identical resonance frequency shift does not exist.

The display unit 660 displays the standard mass extracted by the standard mass extraction unit 650.

The input unit 670 is a user interface for receiving data.

Next, a mass measurement process based on the construction of embodiments of FIGS. 4 and 5, among the construction of above-described embodiments of the present invention, is described.

First, a process of recording resonance frequency shifts $\Delta f_i$ according to the addition of standard masses to correspond to standard masses in the standard mass database DB is described.

Figure 7:
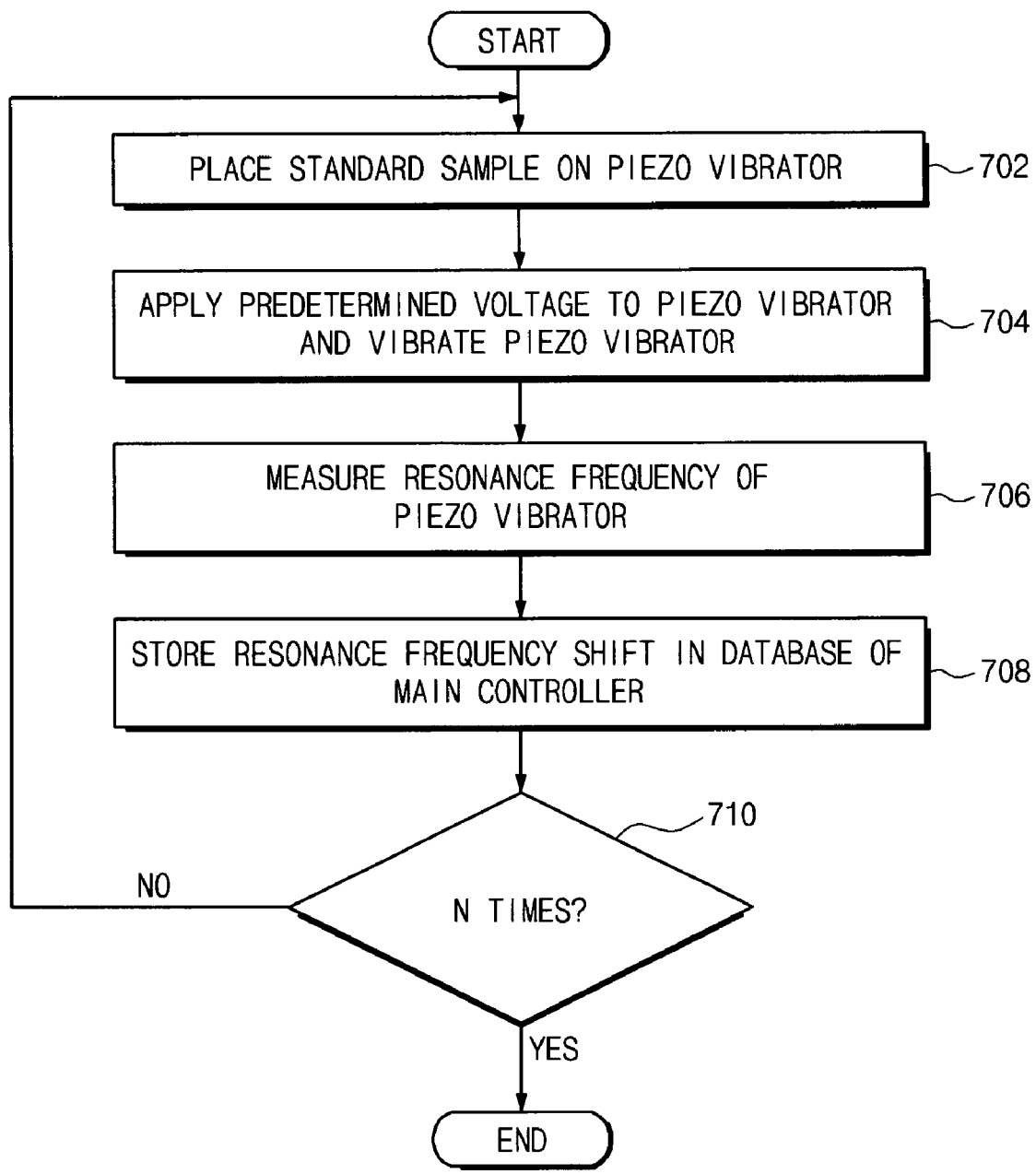
FIG. 7 is a flowchart of a method of constructing a standard mass database according to an embodiment of the present invention.

FIG. 7 is a flowchart of a method of constructing the standard mass database DB according to an embodiment of the present invention.

A standard sample having a standard mass (for example, $m_i$) is contained in the fixing container 104 and fastened to the piezo vibrator 120 at step S702.

The "standard mass" means the mass of the standard sample, which is a known value, as described above.

While the standard sample having standard mass is fastened to the piezo vibrator 120, the control unit 410 of the main controller 150 controls the vibration controller 110 to output a predetermined voltage. The piezo vibrator 120 vibrates at a predetermined resonance frequency (for example, $f_1$) by the predetermined voltage output from the vibration controller 110.

Originally, the piezo vibrator 120 has a natural resonance frequency $f_0$. At this time, if the piezo vibrator 120 vibrates with the standard mass $m_1$ of the standard sample added thereto, the shift of a frequency occurs due to a mass variation (that is, increase in mass). In this case, the resonance frequency is shifted from $f_0$ to $f_1$ at step S704, as described above.

The frequency characteristics at which the piezo vibrator 120 vibrates are measured by the frequency counter 130. The resonance frequency signal measured by the frequency counter 130 is input to and amplified by the signal processor 140, and the amplified signal is converted into a digital signal at step S706.

The resonance frequency signal $f_1$ processed by the signal processor 140 is input to the reception unit 430 of the main controller 150.

As described above, if the reception unit 430 receives the resonance frequency signal $f_1$, the resonance frequency shift $\Delta f_1$ according the addition of standard mass is calculated under the control of the control unit 410, and the calculated resonance frequency shift $\Delta f_1$ is stored in the standard mass database DB to correspond to the standard mass $m_1$ of the standard sample under the control of the control unit 410 at step S708.

Further, steps S702 to S708 are repeatedly performed N times while changing a standard sample (that is, the masses $[m_1,m_2,\Lambda,m_N]$ of a standard sample). Further, resonance frequency shifts $\Delta f_1,\Delta f_2,\Lambda,\Delta f_N$ according to the addition of standard masses and the standard masses $m_1,m_2,\Lambda,m_N$ corresponding thereto are sequentially stored in the standard mass database DB at every repetition cycle.

That is, if it is assumed that the standard mass of a second standard sample is $m_2$, and a calculated resonance frequency shift, obtained by fastening the second standard sample having a standard mass of $m_2$ to the piezo vibrator 120 and repeatedly performing the above steps, is $\Delta f_2$, the calculated resonance frequency shift $\Delta f_2$ is stored in the standard mass database DB to correspond to the standard mass $m_2$.

The range of masses $m_1,m_2,\Lambda,m_N$ of the standard sample must include the mass range of the sample S, which is a measurement object, for example, a range of 0.01 kg to 5 kg. Within this range, a difference between masses is set to a minimum value and a corresponding resonance frequency is measured.

Next, a method of measuring the mass of a sample is described.

Figure 8:
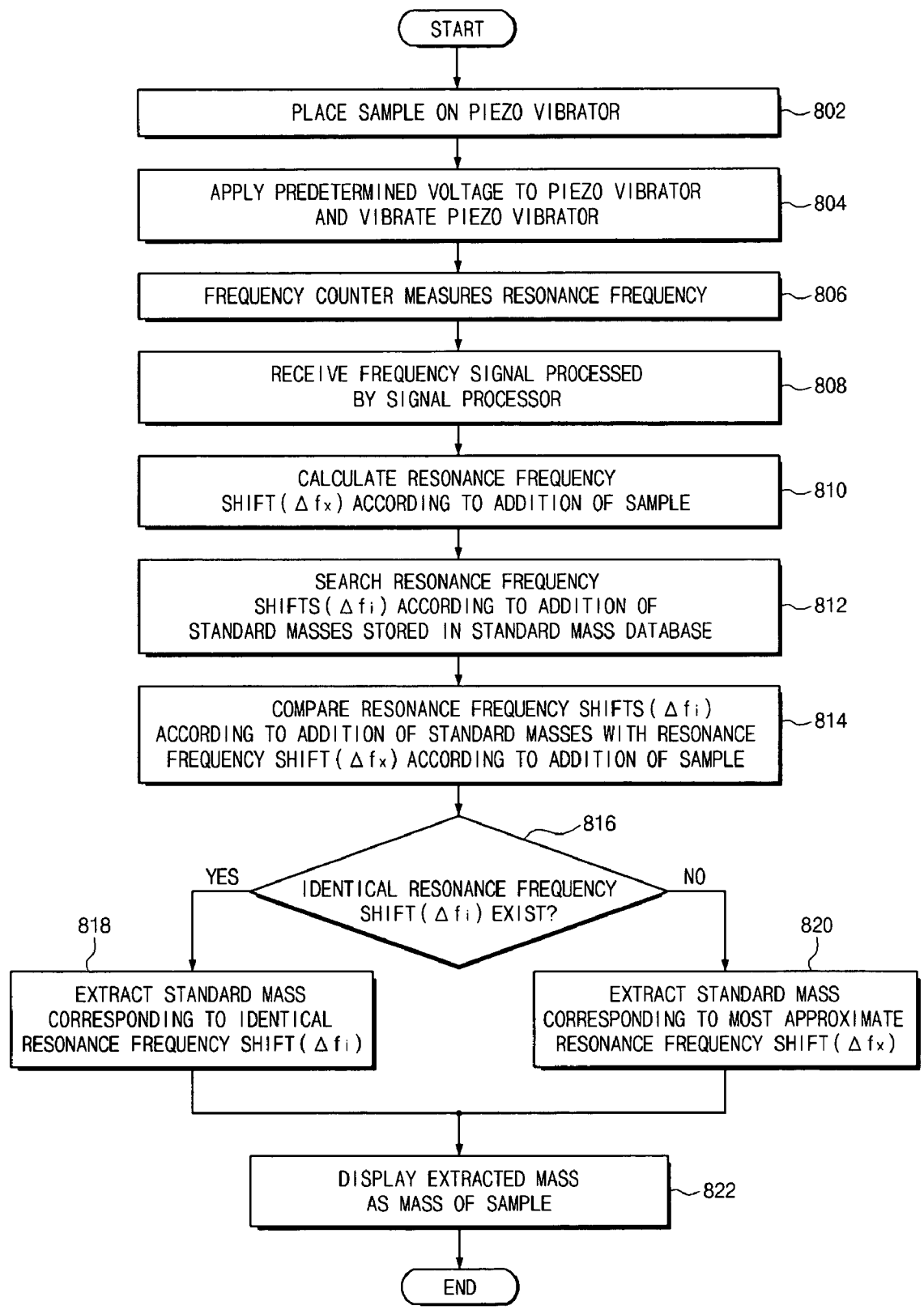
FIG. 8 is a flowchart of a mass measurement method in a gravity-free environment according to an embodiment of the present invention.

FIG. 8 is a flowchart of a mass measurement method in a gravity-free environment according to an embodiment of the present invention.

A sample S is contained in the fixing container 104 and fastened to the piezo vibrator 120 at step S802.

If the vibration controller 110 applies a predetermined voltage to the piezo vibrator 120 under the control of the control unit 410 of the main controller 150 while the sample S is fastened to the piezo vibrator 120, the piezo vibrator 120 vibrates at a resonance frequency $f_x$ at step S804.

The piezo vibrator 120 with the mass of the sample S added thereto has a relatively high frequency, for example, a frequency in a band of several hundreds of kHz. An animal sample, such as a rat, cannot detect such a frequency band.

The resonance frequency of the piezo vibrator 120 is measured by the frequency counter 130 at step S806. The resonance frequency measured by the frequency counter 130 is processed by the signal processor 140, and then input to the reception unit 430 of the main controller 150 at step S808.

If the reception unit 430 receives the resonance frequency $f_x$ of the piezo vibrator 120 according to the addition of the sample S, the control unit 410 reads the program stored in the storage unit 420 and executes commands corresponding to respective modules.

That is, the sample frequency shift calculation module 510 calculates a shift between the resonance frequency $f_x$ and the prestored natural resonance frequency $f_0$ of the piezo vibrator 120, that is, $\Delta f_x = f_0 - f_x$, at step S810.

After the performance of step S810, the standard mass frequency shift search module 520 searches resonance frequency shifts $\Delta f_1,\Delta f_2,\Lambda,\Delta f_N$ according to the addition of standard masses that are stored in the DB and correspond to the standard masses $m_1,m_2,\Lambda,m_N$ and at step S812.

After the performance of step S812, the frequency shift comparison determination module 530 performs a comparison to determine whether a resonance frequency shift identical to the resonance frequency shift value $\Delta f_x$ exists among the searched resonance frequency shifts $\Delta f_1,\Delta f_2,\Lambda,\Delta f_N$ at steps S814 and S816.

After the performance of steps S814 and S816, if one of resonance frequency shift values $\Delta f_{i,j=1,2,\Lambda N}$ according to the addition of standard masses, which is identical to the calculated resonance frequency shift value $\Delta f_x$, exists as a result of determination, the standard mass extraction module 540 extracts a standard mass ($m_3$ in this example) corresponding to the identical resonance frequency shift, for example, $\Delta f_3$, at step S818, and displays the extracted standard mass $m_3$ of the standard sample as the mass of the sample at step S822.

Further, if a resonance frequency shift $\Delta f_i$ according to the addition of standard mass, which is identical to the resonance frequency shift $\Delta f_x$ of the received resonance frequency $f_x$, does not exist, the standard mass extraction module 540 extracts a standard mass corresponding to a value most approximate to the resonance frequency shift $\Delta f_x$, that is, a resonance frequency shift value $\Delta f_i$ having a minimum difference, at step S820, and displays the extracted standard mass as the mass of the sample at step S822.

In the meantime, the scheme of implementing the main controller 150 on the basis of the construction of FIG. 6 and measuring mass using the main controller 150, is similar to the scheme of implementing the main controller 150 for mass measurement according to the embodiment of the present invention on the basis of the construction of FIGS. 4 and 5. This scheme is technology that can be performed by those skilled in the art on the basis of the description of the specification, so that a detailed description thereof is omitted.

In the embodiment of the present invention, a piezo vibrator is used as an electro-dynamic vibrator for generating a natural resonance frequency, but the vibrator of the present invention is not limited to the piezo vibrator. Further, it is apparent that any vibrator for converting an input electrical signal into a dynamic vibration and generating a natural vibration frequency belongs to the technical scope of the present invention. As described above, the electro-dynamic vibrator may be implemented using a quartz vibrator, a ceramic vibrator or a lithium sulphate vibrator.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The mass measurement system and method using the measurement of the frequency shift of a vibrator according to the present invention, having the above construction and operating process, have the following advantages.

First, the mass of a sample is measured on the basis of the comparison of the resonance frequency shift of a piezo vibrator according to the addition of known standard mass with the resonance frequency shift of the piezo vibrator according to the addition of the mass of a sample, thus precisely measuring the mass of the sample.

Second, since the vibration frequency of the piezo vibrator is in a relatively high band of several hundreds of kHz, an animal sample, such as a rat, cannot detect the vibration frequency, so that stress applied to the animal sample during an experiment is reduced, thus increasing the precision of experiments.

Third, since the amplitude of vibration is not high when the piezo vibrator vibrates, little stress is applied to an animal, thus improving the precision of a mass measuring experiment.

Fourth, a vibrator for generating a vibration is implemented with a piezo vibrator, thus decreasing the cost of a mass measurement system.

Fifth, a frequency generator is implemented with a solid electronic device, such as an electro-dynamic vibrator, for example, a piezo vibrator, so as to overcome the mechanical limitation of a conventional mass measurement device. Accordingly, the frequency generator is robust and miniaturized, and mass and space are saved in a spacecraft, such as an international space station, thus increasing the safety of space experiments.

Sixth, the present invention measures an electrical signal output from a frequency counter in real time, so that a measurement time is shortened and repeated measurements are possible, thus improving the precision of measurements.

Seventh, since a "standard mass database" is used, and a main controller can control an entire system, a mass measurement process is automated, thus enabling astronauts to conveniently perform space experiments, and reducing the amount of work and stress of astronauts.

Eighth, the mass measurement system and method of the present invention can measure mass while reducing stress applied to an animal sample, thus greatly contributing to research on biotechnology conducted in an international space station.

What is claimed is:

1. A mass measurement system using measurement of frequency shift of a vibrator, comprising:

a vibrator vibrating at a predetermined resonance frequency with a mass of a sample added thereto;

a frequency counter for measuring a resonance frequency of the vibrator caused by vibration;

a standard mass database for storing therein known standard masses and standard mass frequency shifts corresponding to variation in the standard masses; and a main controller for calculating a sample mass frequency shift corresponding to the added sample mass on the basis of the resonance frequency received from the frequency counter, searching the standard mass frequency shifts stored in the standard mass database, comparing the calculated sample mass frequency shift with the searched standard mass frequency shifts, extracting a predetermined standard mass, outputting the extracted standard mass as the mass of the sample, and controlling the entire system.

2. The mass measurement system according to claim 1, further comprising a vibration controller for outputting a control signal to the vibrator and controlling the vibration of the vibrator under control of the main controller.

3. The mass measurement system according to claim 2, further comprising a signal processor for converting the resonance frequency, which is an analog signal measured by the frequency counter, into a digital signal, and outputting the digital signal to the main controller.

4. The mass measurement system according to claim 3, wherein the vibrator is an electro-dynamic vibrator.

5. The mass measurement system according to claim 4, wherein the electro-dynamic vibrator is any one vibrator selected from among a group including a piezo vibrator, a quartz vibrator, a ceramic vibrator, and a lithium sulphate vibrator.

6. The mass measurement system according to claim 5, wherein the main controller comprises:

a reception unit for receiving the resonance frequency from the signal processor;

a storage unit for storing a program for calculating the sample mass frequency shift on the basis of the resonance frequency received from the reception unit, searching the standard mass frequency shifts, comparing the calculated sample mass frequency shift with the searched standard mass frequency shifts, and extracting the predetermined standard mass;

a control unit for reading the program from the storage unit to execute calculation, search, comparison and extraction, and for controlling the entire system; and a display unit for displaying the standard mass extracted under control of the control unit.

7. The mass measurement system according to claim 6, wherein the storage unit comprises:

a sample mass frequency shift calculation module for calculating the sample mass frequency shift on the basis of the resonance frequency received from the reception unit;

a standard mass frequency shift search module for searching standard mass frequency shifts stored in the standard mass database;

a frequency shift comparison determination module for comparing the calculated sample mass frequency shift with the searched standard mass frequency shifts, and determining whether a standard mass frequency shift identical to the calculated sample mass frequency shift exists among the searched standard mass frequency shifts; and a standard mass extraction module for extracting a standard mass, corresponding to an identical standard mass frequency shift value, as the mass of the sample if the identical standard mass frequency shift value exists as a result of determination, and extracting a standard mass, corresponding to a standard mass frequency shift having a minimum difference with respect to the calculated sample mass frequency shift value, as the mass of the sample if an identical sample mass frequency shift value does not exist.

8. The mass measurement system according to claim 5, wherein the main controller comprises:
   a reception unit for receiving the resonance frequency from the signal processor;
   a sample mass frequency shift calculation unit for calculating the sample mass frequency shift on the basis of the resonance frequency received from the reception unit;
   a standard mass frequency shift search unit for searching the standard mass frequency shifts stored in the standard mass database;
   a frequency shift comparison determination unit for comparing the calculated sample mass frequency shift with the searched standard mass frequency shifts, and determining whether a standard mass frequency shift value identical to the calculated sample mass frequency shift exists among the searched sample mass frequency shifts;
   a standard mass extraction unit for extracting a standard mass, corresponding to the identical standard mass frequency shift value, as the mass of the sample if the identical standard mass frequency shift value exists as a result of determination, and extracting a standard mass, corresponding to a standard mass frequency shift having a minimum difference with respect to the calculated sample mass frequency shift value, as the mass of the sample if an identical standard mass frequency shift value does not exist; and
   a display unit for displaying the extracted standard mass.

9. The mass measurement system according to claim 5, further comprising a fixing container fastened to the piezo vibrator to contain and hold the sample.

10. The mass measurement system according to claim 9, further comprising a support plate that has an area greater than that of the piezo vibrator, is interposed between the piezo vibrator and the fixing container, and is fastened to the piezo vibrator and the fixing container, respectively.

11. A mass measurement method using measurement of frequency shift of a vibrator, comprising the steps of:
   vibrating a vibrator with a mass of a sample added thereto under control of a vibration controller;
   measuring a resonance frequency of the vibrator caused by vibration using a frequency counter;
   calculating a sample mass frequency shift corresponding to the added sample mass on the basis of the measured resonance frequency, searching standard mass frequency shifts that are stored in a standard mass database and correspond to variation in standard masses, and comparing the searched standard mass frequency shifts with the calculated sample mass frequency shift;
   determining whether a standard mass frequency shift identical to the calculated sample mass frequency shift exists among the searched standard mass frequency shifts by comparison;
   extracting a standard mass, corresponding to the identical standard mass frequency shift, as the mass of the sample if the identical standard mass frequency shift exists as a result of determination; and
   displaying the extracted standard mass.

12. The mass measurement method according to claim 11, further comprising the steps of, after the determination step, extracting a standard mass, corresponding to a standard mass frequency shift having a minimum difference with respect to the calculated sample mass frequency shift, as the mass of the sample if an identical standard mass frequency shift does not exist, and displaying the standard mass.

13. The mass measurement method according to claim 12, wherein the standard mass database is constructed by performing the steps of:
   a) vibrating the vibrator with a mass of a standard sample added thereto under control of the vibration controller;
   b) measuring a resonance frequency of the vibrator caused by vibration;
   c) calculating a standard mass frequency shift corresponding to variation in the added mass of the standard sample on the basis of the measured resonance frequency;
   d) recording the calculated standard mass frequency shift to correspond to the standard mass of the standard sample; and
   e) repeatedly performing steps a) to d) N times.

14. The mass measurement method according to claim 11, wherein the standard mass database is constructed by performing the steps of:
   a) vibrating the vibrator with a mass of a standard sample added thereto under control of the vibration controller;
   b) measuring a resonance frequency of the vibrator caused by vibration;
   c) calculating a standard mass frequency shift corresponding to variation in the added mass of the standard sample on the basis of the measured resonance frequency;
   d) recording the calculated standard mass frequency shift to correspond to the standard mass of the standard sample; and
   e) repeatedly performing steps a) to d) N times.

* * * * *

UNITED STATES PATENT AND TRADEMARK OFFICE
CERTIFICATE OF CORRECTION

PATENT NO. : 7,216,543 B2 Page 1 of 1
APPLICATION NO. : 11/180193
DATED : May 15, 2007
INVENTOR(S) : Paik et al.

It is certified that error appears in the above-identified patent and that said Letters Patent is hereby corrected as shown below:

At claim 13, column 12, line 22, after the word "claim", delete "12", and insert --11,--.

At claim 14, column 12, line 37, after the word "claim", delete "11", and insert --12,--.

Signed and Sealed this

Fourth Day of December, 2007

JON W. DUDAS
*Director of the United States Patent and Trademark Office*